United States Patent [19]

Albanese et al.

[11] Patent Number: 5,663,426
[45] Date of Patent: Sep. 2, 1997

[54] SULFONATED PHOSPHINES, PROCESSES FOR THEIR PREPARATION, AND USE THEREOF AS CONSTITUENTS OF CATALYST SYSTEMS

[75] Inventors: Guido Albanese, München; Rainer Manetsberger, Wielenbach; Wolfgang A. Herrmann, Freising, all of Germany

[73] Assignee: Hoechst Aktiengeschaft, Germany

[21] Appl. No.: 538,190

[22] Filed: Oct. 2, 1995

[30] Foreign Application Priority Data

Sep. 30, 1994 [DE] Germany ............ 44 35 189.5

[51] Int. Cl.$^6$ .............. C07C 309/30; C07C 309/32; C07C 309/29
[52] U.S. Cl. .................................................. 562/35
[58] Field of Search .................................... 562/35

[56] References Cited

U.S. PATENT DOCUMENTS

| | | | |
|---|---|---|---|
| 5,451,698 | 9/1995 | Bahrmann | 562/35 |
| 5,481,049 | 1/1996 | Sato et al. | 568/909.5 |

FOREIGN PATENT DOCUMENTS

| | | |
|---|---|---|
| 0632047 | 1/1995 | European Pat. Off. . |
| 0435073 | 7/1991 | Germany . |
| 4410746 | 10/1994 | Germany . |

OTHER PUBLICATIONS

Hermann et al., Angew. chem. Int.Ed. Engl. vol.34., No. 7, 1995, pp. 811–813.

*Primary Examiner*—Nicky Chan
*Attorney, Agent, or Firm*—Bierman, Muserlian & Lucas

[57] ABSTRACT

Sulfonated phosphines of the formula

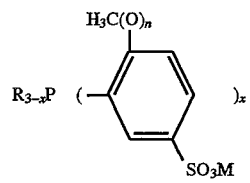

in which R is cyclohexyl or alkyl having 1 to 4 carbon atoms, M is hydrogen, alkyl substituted ammonium, aryl substituted-ammonium, monovalent metal, or the chemical equivalent of a polyvalent metal, x is 1, 2, or 3 and n is 0 or 1. These compounds are obtained by sulfonation of the non-sulfonated parent substances with oleum or an anhydrous mixture of sulfuric acid and orthoboric acid.

18 Claims, No Drawings

SULFONATED PHOSPHINES, PROCESSES FOR THEIR PREPARATION, AND USE THEREOF AS CONSTITUENTS OF CATALYST SYSTEMS

This Application claims the priority of German Application P 44 35 189.5, filed Sep. 30, 1994.

The Invention relates to novel sulfonated phosphines and processes for their preparation, and to the use of these compounds as constituents of water-soluble catalyst systems, in particular for reactions in which C—C bonds are built up.

BACKGROUND OF THE INVENTION

Complex compounds which contain, as the central atom, a metal of group VIII of the Periodic Table of the Elements (IUPAC Version) and, as ligands, P(III) compounds, i.e. phosphines or phosphites and, if appropriate, further groups which are capable of forming complexes, have found increasing use in recent years as catalysts for organochemical syntheses. Thus, the reaction of olefins with synthesis gas to give aldehydes (hydroformylation), which is practiced widely on an industrial scale, is carried out in the presence of catalyst systems which comprise cobalt—and, in particular, rhodium—and triphenylphosphine. Catalysts based on complex compounds containing phosphine have also proven suitable for the reaction of methanol with synthesis gas to give higher alcohols, in particular ethanol and propanol (homologation). In the cases mentioned, the ligands are usually present in excess, so that the catalyst system comprises the complex compound and free ligand. The reactions take place in a homogeneous phase, according to the solubility of the catalysts in organic media.

The reaction can also be carried out in a heterogeneous reaction system. An advantage of this process variant is the easy and gentle separation of the catalyst dissolved in water from the water-insoluble reaction product. The process described in DE-C2 27 00 904 for the preparation of nitriles by addition of hydrogen cyanide to unsaturated organic compounds containing at least one ethylenic double bond operates, for example, in accordance with this principle. For the preparation of aldehydes by reaction of olefins with carbon monoxide and hydrogen, rhodium is employed as metal or in the form of its compounds together with a water-soluble phosphine, for example the alkali metal salt of tri(m-sulfonatophenyl)phosphine, ("TPPTS") as the catalyst according to the process of DE-C2 26 27 354. Further examples of reactions with a heterogeneous catalyst phase are to be found in Angew. Chem. 1993., 105, 1588 et seq.

Although the foregoing two-phase processes have proven to be particularly appropriate on the industrial scale, recent work has perfected them further. An attempt has been made to increase the activity of the catalysts by modification of the complexing ligands and to prolong their activity, in order to reduce the specific catalyst requirements—both for the metal and for the ligand—and therefore the production costs. Economic grounds are also a decisive reason for working towards a significant reduction in the phosphine/metal ratio. Finally, attempts are being made to develop ligand systems which solve individual—e.g. product-specific-problems in the context of known processes. Furthermore, novel fields of use are being sought for these diverse catalyst systems.

SUMMARY OF THE INVENTION

The Invention relates to sulfonated phosphines of the formula

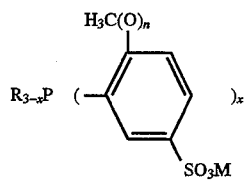

in which R is cyclohexyl or an alkyl radical having 1 to 4 carbon atoms, M is hydrogen, ammonium, alkyl or aryl substituted ammonium, a monovalent metal, or the chemical equivalent of a polyvalent metal, x is 1, 2, or 3, and n is 0 or 1.

The $C_1$ to $C_4$-alkyl radicals represented by R can be straight or branched chain. The dialkyl compounds preferably contain identical alkyl radicals or two cyclohexyl radicals, but compounds with different alkyl radicals or one alkyl and one cyclohexyl radical are not excluded. M is preferably hydrogen, ammonium, tetraalkyl ammonium, alkali metal, in particular sodium or potassium, or the chemical equivalent of an alkaline earth metal, such as magnesium or calcium.

The Invention also relates to a process for the preparation of these phosphines, as well as their use as a constituent of catalyst systems in reactions which lead to the build-up of C—C bonds. Such reactions include hydrodimerization, alkylation of C—H acid compounds, addition reactions on C—C double bonds, and the carbonylation of allyl systems.

Tris(o-tolyl)phosphine, tris(o-methoxyphenyl)phosphine, or derivatives of these compounds in which one or two aryl radicals are replaced by cyclohexyl or alkyl having 1 to 4 carbon atoms are used as starting substances for the preparation of the claimed phosphines. The phosphines are obtained in accordance with J. Org. Chem. 43, 2941 et seq. (1978) by reaction of phosphorus trichloride or alkylchlorophosphines with the Grignard reagent from o-bromotoluene or o-bromomethoxybenzene.

DETAILED DESCRIPTION OF THE INVENTION

The phosphines can be sulfonated without prior purification. According to the Invention, the sulfonating agent used is the anhydrous system of either sulfuric acid/orthoboric acid (at least one mole of orthoboric acid being present per mole of P(III)) or oleum, i.e. a solution of $SO_3$ in sulfuric acid. The $SO_3$ concentration in this solution is expediently 20% to 65% by weight, based on the solution. To avoid the formation of phosphine oxides and to allow higher reaction temperatures, preferably a Lewis acid, for example boric acid, can be added to the oleum in an amount such that at least one mol of boric acid is present per mol of phosphine. The phosphorus compound is introduced portionwise into the system of sulfuric acid/orthoboric acid at 20° to 120° C., or into the oleum at 0° to 20°, preferably from 0° to 5° C. If a Lewis acid is present, the temperature range is 0° to 40°, in particular 0° to 20° C. The sulfonation temperatures are then established while stirring; these are 20° to 350° C., if sulfuric acid/orthoboric acid is used, and not exceeding the temperature ranges stated for the dissolving operation, if oleum is used. The mixture is allowed to after-react for 1 to 3 days.

The sulfonated phosphines are then isolated from the reaction mixture by an extraction/reextraction process. For this, the mixture is diluted with water or, if oleum is used as the sulfonating reagent, preferably with ice, in an amount such that the sulfuric acid concentration in the resulting solution is 0.5% to 50% by weight, preferably 25% to 35% by weight. The hydrolysis product is then extracted with a solution of a water-insoluble amine in a water-insoluble solvent, for example triisooctylamine in toluene, 0.5 to 3 mol of the amine being used per chemical equivalent of sulfonic acid. The sulfonated phosphine passes into the organic phase as the amine salt. By reextraction with an aqueous alkali metal hydroxide solution, it is obtained as an aqueous solution of the corresponding alkali metal salt, from which the phosphine sulfonate is obtained after concentration to dryness.

The novel sulfonated phosphines are colorless powders which dissolve very readily in water. The free acid and the salts of other metals can be prepared from the sodium salts, and also from other alkali metal salts, for example by ion exchange.

The phosphines form complex compounds with various metals and, among these compounds, those with Ni, Pd, and Pt are of particular importance as catalysts for C—C coupling reactions. In this case it is expedient for the metal and phosphorus compound—in the form of its sodium or other water-soluble salt—not to be used in the stoichiometric ratio, i.e. corresponding to the chemical composition of the metal-complex compound originally employed or one which forms under the reaction conditions. It is more advantageous to use an excess of phosphine. The ratio of metal to phosphine can be varied within wide limits, and about 1 to 4 mol of phosphine can be used per mol of metal. A molar ratio of metal to phosphine of 1:1 to 1:2, in particular, 1:2 is preferred.

The metals are employed in elemental form or as compounds. As elements, they are used either in the form of finely divided particles, advantageously colloidally, or precipitated in a thin layer on a support, such as active charcoal, calcium carbonate, aluminium silicate, or alumina. Possible metal compounds are those substances which are water-soluble or become water-soluble under the reaction conditions. The oxides, the salts of inorganic hydrogen and oxygen acids, and the salts of aliphatic mono- and polycarboxylic acids are suitable. Examples of suitable salts are the halides, nitrates, formates, and acetates.

The preparation and the properties of the novel compounds are described below with the aid of selected examples, which are illustrative and not limiting.

EXAMPLE 1

Tris(o-tolyl-m-sulfonic acid)phosphine (a) Preparation of tris(o-tolyl)phosphine Tris(o-tolyl)phosphine is prepared by the process described in J. Org. Chem. 43, 2941 et seq. (1978) by reaction of phosphorus trichloride with the Grignard reagent obtained from o-bromotoluene.

(b) Sulfonation of tris(o-tolyl)phosphine 1.63 g (26.28 mmol) of boric acid is dissolved in 15 ml of concentrated sulfuric acid (96% by weight) in a two-necked flask with an attached dropping funnel, and 2 g (6.57 mmol) of tris(o-tolyl)phosphine is added in small portions to the clear solution. The flask is then cooled to about 5° C. with ice and 27 ml of oleum (65% by weight free $SO_3$) is added dropwise, initially slowly and later faster (i.e. about 1 drop/second), while maintaining this temperature and stirring. When the addition of oleum has ended, the reaction mixture comprises 31.6% by weight of free $SO_3$. The reaction solution is warmed to room temperature and is allowed to after-react for 3 days.

The reaction mixture is then added cautiously, i.e. avoiding temperatures above about 20° C., to ice. The aqueous solution is stirred with a mixture of 69.8 ml of toluene and 65.7 mmol of triisooctylamine for 24 hours. During this procedure, the sulfonated phosphine passes into the organic phase as the amine salt. This is isolated and reextracted with 25% by weight sodium hydroxide solution to isolate the phosphine. The aqueous phase is separated from the amine phase, neutralized if appropriate, and concentrated to dryness with the aid of a rotary evaporator. The resulting crude product can be employed directly as the catalyst component.

To isolate the pure substance, such as is necessary for characterization thereof, the aqueous solution obtained by dilution of the reaction mixture with ice is neutralized with 25% by weight sodium hydroxide solution. The solution is concentrated with the aid of a rotary evaporator until relatively large amounts of sodium sulfate precipitate out. Four times the volume of methanol is then added to the suspension, while stirring intensively, and the sodium sulfate is filtered off. The residue on the filter is rinsed several times with methanol and the filtrates are combined and concentrated to dryness. Thereafter, the residue is taken up with the smallest possible amount of water and the solution is injected into 10 times its volume of methanol, while stirring intensively. The mixture is filtered again and the filtrate is evaporated to dryness in vacuo. For further purification, in particular for removal of the small amount of phosphine oxide present and of undesirable sulfonation products, the product is chromatographed over Sephadex G-25, a three-dimensionally crosslinked polysaccharide (manufacturer: Pharmacia, AB, Uppsala). The yield is 4.02 g, corresponding to 92% of theoretical.

(c) Characterization of trisodium-(o-tolyl-m-sulfonato)phosphine by analysis

| | Elemental analysis calculated for $C_{21}H_{18}Na_3O_9PS_3.4H_2O$ | | | | | |
|---|---|---|---|---|---|---|
| | C | H | P | S | O | Na |
| calculated | 37.55 | 3.72 | 4.61 | 14.32 | 29.53 | 10.27 |
| found | 37.48 | 3.72 | 4.70 | 14.02 | 28.03 | 10.60 |

Spectroscopic data $^{31}$P-{$^1$H}-NMR (161.8 MHz, $D_2O$): δ=−22.8 ppm (s, 1 P)

$^1$H-NMR (250 MHz, $D_2O$): δ=2.27 ppm (s, 9 H, —$CH_3$), 7.17 (dd, $^3J_{HP}$=3.97 Hz, $^4J_{HH}$=1.83 Hz 3 H, H6) 7.35 (dd, $^3J_{HH}$=8.09 Hz, $^4J_{HP}$=4.73 Hz 3 H, H3), 7.79 (dd, $^4J_{HH}$=1.52 Hz, 3 JHP =7.94 Hz, 3 H, H4)

$^{13}$C-{$^1$H}-NMR (100.5 MHz, $D_2O$): δ=146.5 ppm (d, $^3J_{CP}$=25.75 Hz, C5) 141.41 (s, C1) 133.57 (d, $^2J_{CP}$=10.97 Hz, C2), 131.3 (d, $^3J_{CP}$=4.77 Hz, C3), 129.78 (s, C6), 126.88 (s, C4), 20.65 (d, $^3J_{CP}$=20.5 Hz, —$CH_3$)

UV (nm): 226, 272

IR (KBr, cm$^{-1}$): 3056 (v(aryl-H)), 2967, 2575, 222, 1920, 1805, 1637 (sst), 1587 (v(C=C)), 1470, 1446 (aryl-P), 1380, 2000 (sst, br), 1038 (sst), 904, 827.

EXAMPLE 2

Tris(o-methoxy-m-sulfonic acid)phosphine (a) Preparation of tris(o-methoxyphenyl)phosphine Tris(o-methoxyphenyl)phosphine is prepared in an analogous manner to that of J. Org. Chem. 43, 2941 et seq. (1978) for synthesis of tris(o-tolyl)phosphine by reaction of phosphorus trichloride with the Grignard reagent obtained from o-methoxybromobenzene.

(b) Sulfonation of tris(o-methoxybromophenyl)phosphine 1.79 g (28.96 mmol) of boric acid is dissolved in 11.5 ml of concentrated sulfuric acid (96.5% by weight) in a two-necked flask with an attached dropping funnel, and 1 g (2.84 mmol) of tris(o-methoxyphenyl)phosphine is added in small portions to the clear solution. Thereafter, the flask is cooled to about 5° C. with ice and 22 ml of oleum (65% by weight of free $SO_3$) is added dropwise, initially slowly and then faster (i.e. about 1 drop/second), while maintaining this temperature and stirring. When the addition of oleum has ended, the reaction mixture comprises 31.4% by weight of free $SO_3$. The reaction solution is warmed to room temperature and allowed to after-react for 3 days.

The reaction mixture is added cautiously to ice, so that the temperature does not exceed about 20° C. The aqueous solution is stirred with a mixture of 76.95 ml of toluene and 72.4 mmol of triisooctylamine for 24 hours. During this operation, the sulfonated phosphine passes into the organic phase as the amine salt. The phosphine is isolated and reextracted with 25% by weight sodium hydroxide solution. The aqueous phase is separated from the amine phase, neutralized if appropriate, and concentrated to dryness with the aid of a rotary evaporator. The resulting crude product can be employed directly as a catalyst component.

The pure compound is isolated as described in Example 1 by chromatography over Sephadex G-25. The yield is 1.86 g; corresponding to 92% of theoretical.

(c) Spectroscopic characterization of trisodium(o-methoxy-m-sulfonato)phosphine $^{31}P$-{$^1H$}-NMR ($D_2O$): δ=−31.99 (s, 1 P)

$^1H$-NMR ($D_2O$): δ=3.78 (s, 9 H; —$OCH_3$), 7.20 (dd, $^4J_{HP}$=8.9 Hz, $^3J_{HH}$=4.6 Hz, 3 H, H3), 7.24 (dd, $^4J_{HH}$=2.1 Hz, $^3J_{HH}$=4.6 Hz, 3 H, H4), 7.93 (dd, $^4J_{HH}$=2.1 Hz, $^3J_{PH}$=9.6 Hz, 3 H, H6)

$^{13}C$-{$^1H$}-NMR ($D_2O$): δ=56.24 (s, C7), 111.41 (s, C4), 122.17 (d, $^3J_{CP}$=11.5 Hz, C5), 129.31 (s, C6), 131.05 (d, $^3J_{CP}$=2.9 Hz, C3), 136.78 (d, $^2J_{CP}$=1.0 Hz, C1), 163.12 (d, $^2J_{CP}$=14.8 Hz, C2).

EXAMPLE 3

Bis(tert-butyl)(o-tolyl-m-sulfonic acid)phosphine (a) Preparation of bis(tert-butyl)(o-tolyl)phosphine Bis(tert-butyl)(o-tolyl)phosphine is prepared in a manner analogous to that in J. Org. Chem. 43, 2941 et seq. (1978) by reaction of di(tert-butyl)chlorophosphine with the Grignard reagent obtained from o-bromotoluene.

(b) Sulfonation of bis(tert-butyl)(o-tolyl)phosphine 1.63 g (26.28 mmol) of orthoboric acid is dissolved in 9 ml of concentrated sulfuric acid (96% by weight) in a one-necked flask, and 7 ml of oleum (65% by weight of $SO_3$) is added dropwise to provide an $SO_3$ concentration of about 0.6% by weight. The excess $SO_3$ is removed under high vacuum at 60° C. in the course of 45 minutes. 300 mg (1.32 mmol) is bis(tert-butyl)(o-tolyl)phosphine (corresponding to a boric acid/phosphine molar ratio of 20/1) is then added and the mixture is stirred until the phosphine has dissolved. The reaction mixture is heated at 60° C. for 21 hours, then cooled, and hydrolyzed with 20 ml of degassed water.

The aqueous solution is stirred with a solution of 4 ml (9.25 mmol) of triisooctylamine in 30 ml of toluene for 24 hours. To isolate the sulfonated amine, the organic phase is extracted with 25% by weight sodium hydroxide solution and the aqueous phase is separated from the amine phase. The aqueous phosphine sulfonate solution is neutralized and, if appropriate, concentrated to dryness. The resulting crude product can be employed directly as a catalyst component.

The pure compound is isolated as described in Example 1 by chromatography over Sephadex G-25. The yield is 444 mg, corresponding to 95% of theoretical.

(c) Spectroscopic characterization of bis(tert-butyl)(o-tolyl-m-sulfonate)phosphine as the sodium salt $^{31}P$-{$^1H$}-NMR ($D_2O$): δ=16.20 (s, 1 P)

$^1H$-NMR ($D_2O$): δ=1.22 (d, $^3J_{HP}$=12.52 Hz, 18 H, H9), 2.62 (s, 3 H, —$CH_3$), 7.46 (dd, $^3J_{HH}$=8.2 Hz, $^4J_{HH}$=4.3 Hz, 1 H, H4), 7.76 (d, $^3J_{HH}$=8.2 Hz, 1 H, H3), 8.27 (s, 1 H, H6)

$^{13}C$-{$^1H$}-NMR ($D_2O$): δ=23.03 (d, $^3J_{CP}$=24.3 Hz, C9), 29.16 (s, C7), 32.26 (d, $^1J_{CP}$=16.2 Hz, C8), 126.30 (s, C6), 130.72 (d, $^3J_{CP}$=5.7 Hz, C3), 132.25 (d, $^4J_{CP}$=4.3, C4), 135.23 (d, $^2J_{CP}$=10.6 Hz, C2), 140.13 (s, C1), 148.72 (d, $^3J_{CP}$=27.65 Hz, C5).

Although only a limited number of specific examples have been expressly disclosed, it is, nonetheless, to be broadly construed and not to be limited except by the character of the claims appended hereto.

What we claim is:

1. A sulfonated phosphine of the formula

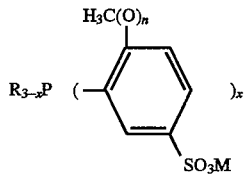

wherein R is independently selected from the group consisting of cyclohexyl and alkyls having 1 to 4 carbon atoms, M is hydrogen, ammonium, alkyl substituted ammonium, aryl substituted ammonium, a monovalent metal, and a chemical equivalent of a polyvalent metal, x is 1 or 2 and n is 0 or 1.

2. The phosphine of claim 1 wherein x is 1 and the R's are identical.

3. The phosphine of claim 1 wherein M is selected from the group consisting of hydrogen, ammonium, tetraalkyl ammonium, alkali metal, and a chemical equivalent of an alkaline earth metal.

4. The phosphine of claim 3 wherein said alkali metal is selected from the group consisting of sodium and potassium.

5. The phosphine of claim 3 wherein said alkaline earth metal is selected from the group consisting of magnesium and calcium.

6. A process for the preparation of the phosphine of claim wherein a compound selected from the group consisting of tris(o-tolyl)phosphine, tris(o-methoxyphenyl)phosphine, and derivatives thereof wherein 1 or 2 aryl radicals are replaced by cyclohexyl or alkyls having 1 to 4 carbon atoms, is reacted with an anhydrous system selected from the group consisting of sulfonic acid/orthoboric acid and oleum, thereby forming a sulfonation mixture, wherein sulfonation of said compound takes place.

7. The process of claim 6 wherein said sulfonation is carried out with sulfuric acid/orthoboric acid at a sulfonation temperature of 20° to 350° C.

8. The process of claim 7 wherein said sulfonation temperature is 20° to 170° C.

9. The process of claim 6 wherein said sulfonation is carried out with oleum.

10. The process of claim 9 wherein said oleum comprises 20% to 65% by weight of sulfur trioxide.

11. The process of claim 10 wherein said oleum comprises a Lewis acid.

12. The process of claim 11 wherein said Lewis acid is boric acid.

13. The process of claim 6 wherein said boric acid is present in an amount which is at least 1 mol per mol of P(III).

14. The process of claim 6 comprising dilution of said sulfonation mixture with water to form an aqueous solution, extraction of said aqueous solution with an extraction solution comprising a water-insoluble amine in a water-insoluble organic solvent, thereby forming an organic phase and an aqueous phase, contacting said organic phase with an aqueous base, separation of said aqueous base including said sulfonated phosphine, from said organic phase, and separating said sulfonated phosphine from said aqueous base.

15. The process of claim 14 wherein said amine is present in an amount of 0.5 to 3 mol per chemical equivalent of sulfonic acid.

16. The process of claim 14 wherein said amine is triisooctylamine.

17. The process of claim 14 wherein said organic solvent is toluene.

18. The process of claim 14 wherein said organic phase is separated from said aqueous phase.

* * * * *